(12) United States Patent (10) Patent No.: US 7,883,503 B2
Kaiser et al. (45) Date of Patent: Feb. 8, 2011

(54) ILLUMINATING BALLOON CATHETER AND METHOD FOR USING THE CATHETER

(76) Inventors: Gary Kaiser, 171 Genius Dr., Winter Park, FL (US) 32789; Gregory L. Mayback, 10313 Bermuda Dr., Cooper City, FL (US) 33026

( * ) Notice: Subject to any disclaimer, the term of this patent is extended or adjusted under 35 U.S.C. 154(b) by 977 days.

(21) Appl. No.: 11/339,258

(22) Filed: Jan. 25, 2006

(65) Prior Publication Data

US 2006/0167439 A1 Jul. 27, 2006

Related U.S. Application Data

(60) Provisional application No. 60/647,204, filed on Jan. 26, 2005, provisional application No. 60/647,205, filed on Jan. 26, 2005.

(51) Int. Cl.
*A61M 27/00* (2006.01)
*A61M 29/00* (2006.01)
*A61F 2/00* (2006.01)
*A61F 13/00* (2006.01)

(52) U.S. Cl. .................. 604/544; 604/96.01; 600/37
(58) Field of Classification Search .................. 604/544, 604/96.01, 20
See application file for complete search history.

(56) References Cited

U.S. PATENT DOCUMENTS 4,248,214 A * 2/1981 Hannah et al. ............... 604/523
4,995,863 A 2/1991 Nichols et al.
6,086,558 A 7/2000 Bower et al.
2001/0037085 A1 * 11/2001 Keith et al. ............... 604/96.01
2005/0080340 A1 * 4/2005 Stewart et al. ............... 600/433

OTHER PUBLICATIONS

Kafali, Hasan, et al.; "Expeditious Method of Urethrovesical Junction Determination in Retropubic Colposuspension with Intraballoon Illumination of Foley Catheter"; Urologia Internationalis; May 2003, vol. 70, pp. 262-264.

* cited by examiner

*Primary Examiner*—Nicholas D Lucchesi
*Assistant Examiner*—Rebecca E Eisenberg
(74) *Attorney, Agent, or Firm*—Mayback & Hoffman, P.A.; Gregory L. Mayback; Katie M. Blakley

(57) ABSTRACT

A directionally limited illuminating balloon catheter includes a multi-lumen shaft having a distal end and a hollow balloon portion disposed at the distal end and inflated through the shaft, the balloon portion having a light source illuminating only a portion of the environment outside the balloon portion. The balloon portion can be have a directionally limited light source directing substantially all illumination towards the shaft. Also provided is a directionally illuminating balloon catheter kit including a set of illuminating catheters each having the light source with different sized illuminating areas to illuminate a different sized partial portion of the environment outside the balloon portion.

26 Claims, 8 Drawing Sheets

ILLUMINATING BALLOON CATHETER AND METHOD FOR USING THE CATHETER

CROSS-REFERENCE TO RELATED APPLICATION

This application claims the benefit under 35 U.S.C. §119(e) of U.S. Provisional Patent Application Nos. 60/647,204 and 60/647,205, filed Jan. 26, 2005; the prior applications are hereby incorporated herein by reference in their entireties.

BACKGROUND OF THE INVENTION

1. Field of the Invention

The present invention relates to a catheter, especially a flexible illuminating balloon catheter and a method for using the catheter.

2. Description of Related Prior Art

A number of conventional balloon catheters exist in the prior art. Some catheters are used to drain the bladder of a patient during surgical procedure or to treat bladder and/or urethra or prostate conditions, for example.

For example, U.S. Pat. No. 4,248,214 to Hannah et al. (hereinafter "Hannah") describes an illuminated urethral catheter for draining the urinary bladder while providing circumferential cold illumination of the adjacent urinary tract. Such illumination enables the surgeon to accurately locate the bladder, junction, and urethra without distorting the same so that, for instance, support sutures may be accurately placed adjacent the urethrovesical junction without injury to the urinary tract. The Hannah catheter emanates light outwardly at its distal end through a fiber optic member in all directions (360 degrees) around its circumference. Thus, the Hannah catheter eliminates the need to orient the fiber optic member angularly within the catheter to provide the desired cold illumination of the urinary tract.

The Hannah illuminated catheter requires the light-emitting surface to extend around the entire circumference of the distal end of the fiber optic so that the need to orient the fiber optic is eliminated. This catheter also has a longitudinally movable fiber optic to move the light-transmitting surface along the catheter tube to a desired location. It is noted that Hannah gives an unclear message regarding the intensity of the light emitted from the proximal-most portion 86 as compared to the ultimate distal tip 82. On col. 6, lines 30 to 32, Hannah indicates that the "intensity of the emitted light increases from portion end 86 to tip 82," i.e., is greater at the proximal end of the emitting area. But at col. 7, lines 50 to 54, Hannah provides that the "intensity of the light emitted from the fiber optic is greatest at the proximal end of abraded portion 84 nearest the light source so that the required high intensity light is provided to illuminate the urethra and urethral-bladder junction."

Hannah teaches that conventional location of the urethrovesical junction by balloon inflation is to be avoided because they "are, at best, imprecise and distort the urinary tract." Hannah at col. 8, lines 40 to 47. It is, therefore, desirable to combine illumination with a balloon catheter to investigate in ways not envisioned by Hannah and areas not envisioned by Hannah. It would be desirable to focus all the illumination at a given place in a patient and in a desired direction so that as much light as possible illuminates the place where the surgeon desires and does not illuminate other areas, which illumination decreases the ability of the surgeon to identify the particular area to be investigated.

For example, a common balloon catheter made by RUSCH® and referred to as a Foley catheter is widely used today for treating and draining a patient's bladder. The Foley catheter is shown in FIG. 1 and has a multi-lumen shaft 1 that is disposed in the urethra 10. A balloon portion 3 is disposed at the distal end of the shaft 1, a fluid drain section 4 is disposed at the distal end of the balloon 3, and a curved, distal guiding tip 5 is disposed at the distal-most end of the entire catheter. When placed properly, the proximal-most side of the inflated balloon 3 rests on the interior wall 31 of the bladder 30, entirely blocking off the urethrovesical junction 11 connecting the bladder 30 and the urethra 10. In such a position, the fluid drain section 4 allows continuous drainage of the bladder 30 and the balloon 3 virtually entirely prevents the catheter from slipping out of the bladder. This ideally inserted position is shown in FIG. 1.

It is noted that use of the word "proximal" in the instant application refers to a direction towards the physician, which also corresponds to the bottom of the figures of the drawings.

As such, use of the word "distal" in the instant application refers to a direction away from the physician, which also corresponds to the top of the figures of the drawings.

As used herein, a fluid can be both a liquid and a gas. Exemplary fluids for inflating a balloon 3 are saline, air, or carbon dioxide gas. Exemplary fluids drained by the catheters mentioned herein include urine and blood.

For placement of this catheter in the ideal position within the bladder 30, however, the physician or technician has no visual aid. As diagrammatically illustrated in FIG. 1, the wall 40 defining the urethrovesical junction 11 is very short in the longitudinal direction of the urethra 10. If the technician, nurse, or physician inserts the catheter too far into the bladder 30, no damage occurs from balloon inflation; however, there is a possibility of leakage around the balloon 3, which helps to lubricate the urethra 10 such that gentle proximal movement places the proximal side of the balloon 3 against the urethrovesical junction 11. The bladder 30 can then easily expand and stretch to compensate for the balloon 3. A normal bladder capacity is 400 to 500 cc. A normal balloon capacity is approximately 10 to 12 cc although larger balloons are sometimes used.

The complication occurs when the technician and/or nurse inflates the balloon and in fact the balloon is not in the bladder. If the technician does not insert the catheter in far enough, then the balloon 3 will be subsequently inflated within the urethra 10—a condition that is common and, not only is it to be avoided at all costs, is a frequent cause of bladder infections created during a hospital or clinic visit. Infections arise because inflation of the bladder 3 inside the urethra 10 causes the urethra 10 to stretch too far. Even though the urethra 10 is a flexible tube, it has limits to which it can be safely stretched from within. Almost every balloon catheter has an outer diameter/circumference that well-exceeds the safe stretching limit of the urethra 10. Therefore, if the balloon catheter is not inserted far enough, inflation of the balloon 3 will cause serious injury to the urethra 10. This is especially true with elderly patients who have urethra 10 that are not as elastic as younger patients. Tearing of the urethra 10 in this way causes bleeding and allows bacteria to enter into the bloodstream at the tear site, thus causing the subsequent bladder infection.

In such a case, the balloon expands and tears the surrounding membrane called the mucosa. Tearing of the urethra 10 in this way causes bleeding and allows bacteria to enter into the bloodstream at the tear site, thus causing the subsequent bladder infection. Significant bleeding can become life threatening. The urethra can normally dilate several millimeters; however, when the balloon is inflated, this dilation is usually several centimeters.

Over 96 million indwelling catheters are sold on an annual basis. Twenty four million catheters are sold to hospitals in the U.S. There are numerous complications associated with those catheters that need to be prevented. These complications are responsible for increases in hospital stays, excessive bleeding, mortality, as well as morbidity. This also causes an increased expense and burden on the already-stressed health care system.

The complications result from several different mechanisms. First, and probably most common, is improper placement of the catheter. Because of the unique anatomy of the male urethra, placing a urethral catheter for urinary drainage can be difficult. A problem arises when the physician, technician, or nurse thinks that the catheter is actually in proper position. The proper position for the catheter is with the balloon being in the cavity of the bladder and the tip distal to the balloon is used to drain the bladder cavity.

Life threatening bleeds, especially in patients who are anti-coagulated, can and do occur. Also when the urine is infected, as in immunocompromised patients and the elderly, the bacteria, then, get into the blood stream and can cause serious infections called sepsis, which frequently can lead to death. If the patient survives the initial trauma, then long-term complications, such as strictures, can and usually do occur. Strictures are narrowings within the urine channel and usually require additional procedures and surgeries to correct.

Other mechanisms of catheter-induced injuries are inadvertent manipulation of the tubing or dislodging of the balloon because the balloon is pulled due to a sudden jerk or tension. This usually happens when the patient is ambulating or traveling from the bed to the commode or bathroom. The tubing may inadvertently become fixed while the patient is still moving, at which time a sudden jerk is imparted upon the balloon and pulls the balloon into the urethra causing severe pain and bleeding. Injury caused by the improper, inadvertent, and/or early removal of an inflated balloon catheter is referred to as iatrogenic injury (also referred to as an in-hospital injury).

Yet another scenario occurs when the patient deliberately pulls on the catheter, thereby causing self-induced pain and injury to the urethra. This commonly happens in confused patients, for example, patients in nursing homes who have a disease or cognitive dysfunction problem, such as Alzheimer's disease, or other diseases that make the patient unable to understand the necessity of having a catheter. Confusion occurs when the patient has a spasm causing a strong urge to urinate and pain. During the spasm, the confused patient often tugs and pulls on a catheter, which results in injury.

These types of injuries are not limited to males and also cause severe damage to the female bladder and urethra. The injuries can also occur post-surgically, which makes the damage even more severe. One common situation where injury is cause is when the patient is medicated with morphine or other analgesics that render the patient confused and unable to make rational decisions. These injuries have been well documented and are not limited to adults. Numerous injuries are documented in pediatric patients.

Usually, it takes time to make a diagnosis of patient-caused catheter injury. Immediately after diagnosing the injury, a technician needs to deflate the catheter. However, once the urethra is torn, replacing the damaged catheter with another catheter is quite difficult and, in fact, exacerbates the injury. Sometimes, the patient has to be taken to the operating room to replace a urinary drainage tube once this scenario occurs. Because catheters and leg bags are now used routinely in certain situations during home health care, this scenario is not limited to hospitals and occurs at nursing homes or the patient's home.

Most of the recent catheter technology has been focused on reducing urinary tract infections that are caused by catheters, injuries that are usually the most common catheter-related complications.

A balloon catheter made by TherMatrx, Inc. is used to treat Benign Prostatic Hyperplasia by treatment with THERMATRX® Dose Optimized Thermotherapy, a minimally invasive procedure performed in a urologist's office that uses heat delivered through a microwave antenna. A urethral catheter containing the microwave antenna is passed through the urethra and prostate gland and is secured by a balloon at the tip of the catheter that passes through the urethral sphincter. Localized microwave energy is delivered at a temperature high enough to relieve BPH symptoms, including difficult, frequent, or urgent urination. Features of such a catheter are also diagrammatically illustrated in FIG. 1. The catheter differs from the standard Foley catheter by the addition of a radiation coil 2 disposed at a distal end of the shaft 1 proximal to the balloon 3. When placed properly, the radiation coil 2 is immediately adjacent and/or inside the prostate 20 and the proximal-most side of the inflated balloon 3 rests on the interior wall 31 of the bladder 30, entirely blocking off the urethrovesical junction 11. In such a position, the prostate 20 can be directly treated with the radiation coil 2. This ideally inserted position is shown in FIG. 1. In use, correct placement of this catheter in the ideal position within the bladder 30 and near the prostrate 20 is the same as the Foley catheter—it is difficult and gives the physician or technician no visual aid. If the balloon 3 of the THERMATRX® catheter is not at the urethrovesical junction 11, then the heating element 2 would not be in the proper position and subsequent heat damages an undesired area that can cause unintended injury.

In a conventional balloon 3, the balloon 3 has a substantially constant balloon wall thickness. The balloon 3 is fixed to the outer surface of a fluid drainage line (not illustrated in FIG. 1) and is not intended to be removed therefrom or to burst thereon unless an extraordinary amount of inflation occurs. If such an event happens, the material of the balloon will open at a random location based upon the microscopic fractures or weaknesses in the material itself. Such a tearing event is not supposed to occur under any circumstances during use with a patient.

Prior art catheters are not constructed to prevent tearing of the urethra during a catheter implanting procedure and are not constructed to break in any predefined way. Accordingly, it would be beneficial to provide a balloon catheter that does not inflate past the tearing limit of a urethra and breaks in a desired, predefined way under certain conditions.

In a conventional balloon 3, the balloon 3 has a substantially constant wall opaqueness—it is either fully transparent or it is semi- or fully-opaque (due to the natural properties of the balloon material). Accordingly, it would be beneficial to provide a balloon catheter that has differently placed regions of reflectivity and/or opaqueness to direct illumination from within the balloon catheter in a desired direction.

SUMMARY OF THE INVENTION

It is accordingly an object of the present invention to provide a pressure-limiting balloon catheter and method for using the catheter that overcome the hereinafore-mentioned disadvantages of the heretofore-known devices and methods of this general type and that does not inflate past the tearing limit of a lumen in which the catheter is placed, for example, in the urethra, and quickly and rapidly deflates if pulled out prior to deflation of the balloon.

The purpose of the breakaway catheter of the present invention is to prevent injury by having the balloon automatically deflate before an injury can occur. While the catheter of the present invention makes it a safer device for urinary drainage, the present invention can also be used for any procedures in which balloons are used to dilate cavities. Examples of these procedures include coronary artery vessels, peripheral vascular vessels, such as the aorta and extremity vessels. Balloon dilations of other lumens, such as ureters and the esophagus, are also candidates for use of the catheter of the present invention.

Although deflation of a catheter renders it useless, deflation protects the patient from serious harm. Prevention of such injuries is becoming more and more important because the injuries are commonplace. The increase occurs for a number of reasons. First, a greater percentage of the population is aging. Second, there is a current trend to use less-skilled health care personnel to perform more procedures and to be responsible for treatment, both of which save money. The shortage of nursing professionals (R.N.s) exacerbates this trend. The present tendency is to use nursing professionals for more functions, such as administration and delivery of medications. This leaves only the less-skilled technicians with the task of inserting catheters and taking vital signs. Under such circumstances, more injuries are likely. Lastly, catheter-related complications are becoming more severe due to the increased use of anticoagulation medication, such as Plavix™, that is frequently prescribed in treating cardiovascular disease.

Yet another possible complication arising from the standard Foley catheter is that the balloon will not deflate even when the deflation mechanism is activated. This situation can occur, for example, because the wrong fluid is used to inflate the balloon, such as saline, which can crystallize. Sometimes, the ability to deflate the catheter is interrupted because the drainage channel that is used to deflate the balloon becomes obstructed, which is common if the catheter is left in place too long. Remedy of such a scenario involves an invasive procedure, which includes threading a needle or other sharp object somewhere through the body cavity to puncture the balloon and, thus, dislodge the catheter.

With the breakaway catheter or auto-deflating balloon of the present invention, the technician, nurse, or doctor merely needs to actuate the deflation valve or pull on the catheter to cause the catheter to automatically deflate, thus sparing the patient from any additional surgical procedures.

The added benefit of the present invention is not just for safety, significant financial benefits arise as well.

It is believed that catheter-induced injuries are much more common than public documentation suggests. Catheter-related trauma occurs roughly at least once a week in a large metropolitan hospital. Usually, each incident not only increases the patient's hospital stay substantially, but also the expense of the stay. Each incident (which is usually not reimbursed by insurances) can increase the cost to the hospital thousands, even tens of thousands of dollars.

When additional surgery is required to fix the catheter-induced injury, increased expense to the hospital is not only substantial, if litigation occurs as a result of the injury, damages awarded to the patient can run into the millions of dollars. The catheter of the present invention, therefore, provides a safer catheter that has the possibility of saving the medical industry millions of dollars.

To prevent occurrences of urethra tearing due to premature-improper inflation of the balloon and/or due to premature removal of an inflated balloon, the invention of the instant application provides a balloon safety valve.

The maximum stress that a typical urethra can take without tearing and/or breaking is known and is referred to as a maximum urethra pressure. It is also possible to calculate how much pressure is exerted upon the exterior of a balloon of a balloon catheter by measuring the pressure required to inflate the balloon. Knowing these two values, it is possible to construct a balloon that breaks rapidly and/or ceases inflation if the maximum urethra pressure is exceeded.

For example, in a first embodiment, the balloon, which is typically some kind of rubber, silicone, or plastic, can be made with a breaking point that instantly deflates the balloon if the pressure in the balloon exceeds the maximum urethra pressure. It is acknowledged and accepted that, once the balloon breaks, this catheter is useless and must be discarded because the cost of injury far outweighs the cost of the disposable catheter. Also, such a balloon is limited to inflation with a bio-safe fluid to prevent unwanted air/gas from entering the patient. If, however, air will not injure the patient, the fluid can be air.

As an alternative to a one-use breaking safety valve, a multi-use pressure valve can be added to the balloon inflation lumen and can be set to open into the environment (instead of in the patient) if the maximum urethra pressure exceeded in the balloon or the balloon inflation lumen. Such a valve can be located near or at the balloon inflation port and, in such a configuration, will not enter improperly the patient. Any combination of the above valves is envisioned as well.

With the foregoing and other objects in view, there is provided, in accordance with the invention, a breakaway catheter, including a multi-lumen shaft having a distal end, a hollow balloon portion disposed at the distal end of the shaft, the balloon portion having a distal end and an interior, and at least one of the shaft and the balloon portion having a balloon safety valve formed to open to the environment outside the at least one of the shaft and the balloon portion when greater than a given bursting pressure exists within at least one of the shaft and the interior of the balloon portion.

In accordance with another feature of the invention, the shaft defines a fluid drain lumen and a balloon inflation lumen fluidically connected to the interior of the balloon portion, and the balloon safety valve is formed to open to the environment outside at least one of the shaft and the balloon portion when greater than a given bursting pressure exists within at least one of the balloon inflation lumen and the interior of the balloon portion.

In accordance with a further feature of the invention, the shaft has a proximal end defining a balloon port fluidically connected to the balloon inflation lumen and an inflating connector is fluidically connected to the balloon inflation lumen through the port.

In accordance with an added feature of the invention, the inflating connector is at least a portion of a luer connector.

In accordance with an additional feature of the invention, the proximal end of the shaft defines a fluid port fluidically connected to the fluid drain lumen.

In accordance with yet another feature of the invention, there is provided a fluid drain disposed at the distal end of the balloon portion and fluidically connecting the fluid drain lumen to the environment at the fluid drain and the fluid port to the environment at the proximal end of the shaft.

In accordance with yet a further feature of the invention, the fluid drain has a curved, distal guiding tip.

In accordance with yet an added feature of the invention, the balloon safety valve is at the balloon portion and is fluidically connected to the interior of the balloon portion.

In accordance with yet an additional feature of the invention, the balloon safety valve is integral with the balloon portion.

In accordance with again another feature of the invention, the balloon safety valve is at the shaft and is fluidically connected to the interior of the balloon portion.

In accordance with again a further feature of the invention, the balloon safety valve is integral with the shaft.

In accordance with again an added feature of the invention, the balloon safety valve is removably attached to the shaft.

In accordance with again an additional feature of the invention, the balloon inflation lumen and/or the balloon portion has a material breaking point formed to break and deflate the balloon portion when pressure in at least one of the balloon inflation lumen and the balloon portion exceeds the given pressure.

In accordance with still another feature of the invention, the given pressure is a maximum urethra pressure.

In accordance with still a further feature of the invention, the balloon portion has a wall thickness and the balloon safety valve is a defined reduction in the wall thickness.

In accordance with still an added feature of the invention, the reduction has a shape selected from one of the group consisting of a hemisphere, a cylinder, a groove, a trapezoid, a triangle, a square, a rectangle, a pyramid, and frusto-conical. If the reduction is a groove, then the groove can be formed to extend partly around the balloon portion.

In accordance with still an additional feature of the invention, the shaft defines a balloon inflation lumen fluidically connected to the interior of the balloon portion, the shaft has an outer surface, and the defined reduction is a narrowing of a wall thickness between the balloon portion and the environment and/or the balloon inflation lumen and the outer surface of the shaft.

In accordance with another feature of the invention, the balloon inflation lumen and the outer surface define a wall therebetween, and the defined reduction is a narrowing of a thickness of the wall from the outer surface towards the balloon inflation lumen and/or from the balloon inflation lumen towards the outer surface.

In accordance with a further feature of the invention, the shaft has a wall thickness and the balloon safety valve is a defined reduction in the wall thickness.

In accordance with an added feature of the invention, the balloon safety valve opens into the environment and/or a patient when broken.

In accordance with an additional feature of the invention, the balloon safety valve is formed to burst at a first breaking force less than a second breaking force required to burst at least one of the balloon portion and the shaft.

In accordance with yet another feature of the invention, at least one of the balloon portion and the shaft is formed to burst at a first breaking force and the balloon safety valve is formed to burst at a second breaking force less than the first breaking force.

With the objects of the invention in view, there is also provided a breakaway catheter, including a multi-lumen shaft having a distal end, a hollow balloon portion disposed at the distal end of the shaft, the balloon portion having a distal end and an interior, and at least one of the shaft and the balloon portion having a balloon safety valve formed to burst at a first breaking force less than a second breaking force required to burst at least one of the balloon portion and the shaft.

With the objects of the invention in view, there is also provided a pressure-limiting balloon catheter, including a multi-lumen shaft having first and second lumen each shaped to pass a respective fluid therethrough, a hollow balloon portion defining an interior chamber fluidically connected to the first lumen for receiving fluid therein to inflate and deflate at least a part of the balloon portion, and a pressure-limiting valve fluidically connected to at least one of the balloon portion and the first lumen, the valve opening to the environment of at least one of the shaft and the balloon portion when greater than a given bursting pressure exists in the least one of the balloon portion and the first lumen.

With the objects of the invention in view, there is also provided a pressure-limiting balloon catheter, including a multi-lumen shaft having a balloon inflation lumen shaped to pass a balloon-inflating fluid therethrough and a catheter lumen shaped to pass a fluid therethrough, a hollow balloon portion defining an interior chamber fluidically connected to the balloon inflation lumen for receiving the balloon-inflating fluid therein to inflate and deflate at least a part of the balloon portion, and a pressure-limiting valve fluidically connected to at least one of the balloon portion and the balloon inflation lumen, the valve opening to the environment of at least one of the shaft and the balloon portion when greater than a given bursting pressure exists in the least one of the balloon portion and the balloon inflation lumen.

With the objects of the invention in view, there is also provided a breakaway catheter kit, including a set of breakaway catheters according to the present invention, each of the catheters having the balloon safety valve with different safety valve breaking constants.

It is accordingly a further object of the present invention to provide an illuminating balloon catheter and method for using the catheter that overcome the hereinafore-mentioned disadvantages of the heretofore-known devices and methods of this general type and that focuses a substantial amount of illumination at a given place in a patient and in a desired direction so that as much light as possible illuminates the place where the surgeon desires and does not illuminate other areas and to do so with a balloon of a balloon catheter.

The present invention relates to a catheter that has a light system incorporated therein that illuminates the organ from the inside. For example, a urethra balloon catheter can have a light source on the balloon and, when the balloon is inflated in the bladder and the light is turned on, the inflated bladder acts as a light source having a relatively spherical shape dependent upon the directionality of the light source (uni-directional, multi-directional, omni-directional).

As described above, Hannah uses omni-directional light for locating the urethrovesical junction in a gynecological procedure referred to as the Marshall-Marchetti-Kranz (MMK) procedure. While it is true that some prior art devices like Hannah use illumination to identify regions in a patient, they do not combine directional illumination with a balloon catheter because, to do so, would not allow the prior art devices to perform their intended purpose—eliminate the need to orient the fiber optic angularly within the catheter. Specifically, these devices do not and cannot focus light in a particular desired direction, i.e., they only provide omni-directional illumination.

The invention of the instant application provides directionally guided illumination of a balloon catheter when inside a patient. When a physician is operating on a bladder or a prostate, for example, it is difficult to locate particular areas on the organ that are of interest to the physician. One example procedure requires the location of the junction between the prostate and the bladder, referred to as the urethrovesical junction. Typical operations for the bladder and prostate are laparoscopic, meaning that a small incision is made in the torso of the patient and instruments are inserted through these incisions for carrying out the operation. The physician, therefore, remotely operates on the organ using a viewing system inserted through the incision. Sometimes, the light shining from one part of the laparoscope is insufficient for locating a desired area, primarily because it is shining the light from outside the urethra, prostate, and bladder. Thus, reflection and tissue density prevent optimal location of a desired tissue region. It would be desirable, in some instances, to improve upon such lighting measures.

The balloon catheter according to the invention lights the organ from the inside (preferably, while lowering or shutting off the light of the laparoscope) and, therefore, gives the physician a different perspective. In such a case, the physician sees structures in and/or on the hollow organ, but illuminated from within the organ. Interior lighting allows the physician to better locate the urethrovesical junction.

When prostate cancer is detected in a patient, a laparoscopic prostatectomy is carried out to remove the prostate and seminal vesicles. It is self-evident that, during a laparoscopic prostatectomy, it is critical to identify the junction between the prostate and the bladder because error in detecting the junction may result in undesired removal of necessary body tissue. Failure to identify the urethrovesical junction clearly, therefore, is quite serious. Performing the procedure correctly requires clear identification of the urethrovesical junction without error. If the prior art omnidirectional illuminating devices are used, the light emitting in all directions except towards the urethrovesical junction diminishes the ability of the physician to carry out the laparoscopic prostatectomy.

With the invention of the instant application, the ability to location the junction is improved, not diminished. The illuminating balloon of the present invention is inflated in the bladder and the surgeon or assistant rotates the catheter using the directional light to help locate this junction, in a similar way to illumination from a lighthouse.

Inflation of the balloon to have the proximal portion thereof press against the wall of the bladder near the urethrovesical junction to compress the tissue there allows the urethrovesical junction to be very apparent when viewed through a laparoscope. In combination with the compression of the urethrovesical junction, the directed illumination from the fiber optic according to the present invention allows the metes and bounds of the urethrovesical junction to be clearly identified. Accordingly, success rates of laparoscopic prostatectomy, for example, will increase.

The light source can either be inside the balloon (in which case at least a portion of the balloon corresponding to the light-emitting area is transparent), on the balloon surface, or near the tip of the catheter distal of the balloon. The present invention combines the inflation of the balloon with the directional illumination to illuminate areas during surgical procedures.

In one embodiment of the illuminating catheter of the present invention, portions of the balloon can have a reflective coating so that light is directed (in the manner of a lighthouse) only in a given direction, or a set of given directions.

When a Foley catheter (or other urethral catheter) is inserted properly for a laparoscopic prostatectomy, the urethrovesical junction should be directly opposite the tip 5 of the catheter. In such a configuration, it is desirable if all the illumination is directed back towards the shaft 1 (in a proximal direction) and illumination in the distal direction is entirely prevented. Thus, a reflective coating is placed on the inside or outside surface of the balloon such that, when the balloon is inflated and is illuminated from within, all illumination is directed proximally.

A hemispherical coating is one variant for proximally directing such illumination. Depending on the lateral distance away from the urethrovesical junction that the physician wishes to view, the reflective coating can be merely present on the distal hemi-spherical half of the balloon or it can extend further in the proximal direction along the surface of the balloon. For example, the reflective surface can be disposed on ⅔rds of the sphere of the balloon such that only ⅓ of the surface area of the balloon allows illumination in the proximal direction.

Further, because the physician views the urethrovesical junction from only one side thereof, there may not be a need to illuminate the "back" half of the urethrovesical junction with respect to the viewing side of the physician. In other words, there is a need to only view the "front" side with the illumination—the side of the urethrovesical junction at which the physician is looking. In such a case, the urethrovesical junction will be illuminated particularly well to the exclusion of all other prostate-urethra-bladder structures if the directional illumination catheter of the present invention is used.

The reflective surface of the present invention can be disposed on the interior of the balloon or on the exterior thereof, or both. Also, instead of a reflective coating, the balloon can have a substantially opaque portion and a substantially transparent portion—the latter being disposed at the balloon to direct illumination in the desired direction and the former being disposed at the balloon such that light does not emanate in any direction at which illumination is not desired. In such a configuration, the reflective surface can be complemented with or separate from the opaque/transparent configuration. For example, the reflective surface can be in the interior of the balloon with a transparent portion corresponding to/aligned with the balloon portion not having the reflective surface and with an opaque portion corresponding to the location/surface area of the reflective surface.

These lighting systems can be articulated (i.e., rotationally displaced) so that the physician can adjust the direction of the light.

Many lighting configurations are possible. One example configuration includes a fiber optic strand or bundle of strands that terminate in the balloon, similar to the single strand of Hannah. Accordingly, U.S. Pat. No. 4,248,214 to Hannah et al. is herewith incorporated by reference herein in its entirety. Another example includes a light-emitting diode (LED) disposed in or on the balloon.

With the foregoing and other objects in view, there is provided, in accordance with the invention, a directionally illuminating balloon catheter, including a multi-lumen shaft having a distal end and a hollow balloon portion disposed at the distal end and inflated through the shaft, the balloon portion having a light source illuminating only a portion of the environment outside the balloon portion.

With the objects of the invention in view, there is also provided a directionally illuminating balloon catheter, including a multi-lumen shaft having a distal end and a hollow balloon portion disposed at the distal end and inflated through the shaft, the balloon portion having a directionally limited light source.

With the objects of the invention in view, there is also provided a directionally illuminating balloon catheter, including a multi-lumen shaft having a distal end, and a hollow balloon portion disposed at the distal end and inflated through the shaft, the balloon portion having a light source directing substantially all illumination towards the shaft.

With the objects of the invention in view, there is also provided a catheter kit, including a set of directionally illuminating catheters, each of the catheters having the light source with different sized illuminating areas to illuminate a different sized partial portion of the environment outside the balloon portion.

In accordance with another feature of the invention, the balloon portion has an interior, and the shaft defines a fluid drain lumen and a balloon inflation lumen fluidically connected to the interior of the balloon portion.

In accordance with a further feature of the invention, the light source is connected to the interior of the balloon portion through at least one of the fluid drain lumen and the balloon inflation lumen.

In accordance with an added feature of the invention, the shaft further defines an illumination device lumen and the light source is connected to the interior of the balloon portion through the illumination device lumen.

In accordance with an additional feature of the invention, the shaft has a proximal end defining a balloon port fluidically connected to the balloon inflation lumen and an inflating connector is fluidically connected to the balloon inflation lumen through the balloon port.

In accordance with yet another feature of the invention, the inflating connector is at least a portion of a luer connector.

In accordance with yet a further feature of the invention, the proximal end of the shaft defines a fluid port fluidically connected to the fluid drain lumen.

In accordance with yet an added feature of the invention, the balloon portion has a distal end and a fluid drain is disposed at the distal end of the balloon portion and fluidically connects the fluid drain lumen to the environment at the distal end. The fluid drain can have a curved, distal guiding tip.

In accordance with yet an additional feature of the invention, the light source illuminates only approximately a proximal half of the environment outside the balloon portion.

In accordance with again another feature of the invention, the light source illuminates only approximately half of the proximal half of the environment outside the balloon portion.

In accordance with again a further feature of the invention, the light source only illuminates a partial asymmetrical portion of the environment outside the balloon portion.

In accordance with again an added feature of the invention, the balloon portion has different regions of reflectivity and opaqueness to direct illumination from within the balloon portion into a given area outside the balloon portion.

In accordance with again an additional feature of the invention, the balloon portion is of a material and the regions of reflectivity and opaqueness are a natural property of the material.

In accordance with still another feature of the invention, the balloon portion has an at least semi-transparent portion for transmitting light out from the balloon portion through the transparent portion and an opaque portion for preventing transmission of light out from the balloon portion through the opaque portion.

In accordance with still a further feature of the invention, the balloon portion has a proximal side facing the shaft, the shaft and the balloon portion form a urethral catheter, and the light source illuminates substantially only a urethrovesical junction when the proximal side of the balloon portion is adjacent the urethrovesical junction.

In accordance with still an added feature of the invention, the light source is inside and/or outside the balloon portion.

In accordance with still an additional feature of the invention, the balloon portion has an interior, and at least one portion of the interior has a reflective coating to direct light emanating from the balloon portion.

In accordance with another feature of the invention, the coating is integral with the balloon portion.

In accordance with a further feature of the invention, the coating is disposed on the balloon portion.

In accordance with an added feature of the invention, the light source directs substantially all illumination towards the shaft.

In accordance with an additional feature of the invention, the light source transmits substantially no illumination out from the balloon portion opposite the shaft.

In accordance with yet another feature of the invention, the balloon portion has an interior and the light source rotates within the interior of the balloon portion in the manner of a lighthouse.

In accordance with yet a further feature of the invention, the light source directs light only in a given direction.

In accordance with a concomitant feature of the invention, the light source is selected from at least one of the group consisting of a fiber optic, a light-emitting diode, an organic light-emitting diode, and a combination of the fiber optic, the light-emitting diode, and the organic light-emitting diode.

Other features that are considered as characteristic for the invention are set forth in the appended claims.

Although the invention is illustrated and described herein as embodied in an illuminating balloon catheter and method for using the catheter, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

DETAILED DESCRIPTION OF THE PREFERRED EMBODIMENTS

Figure 1:
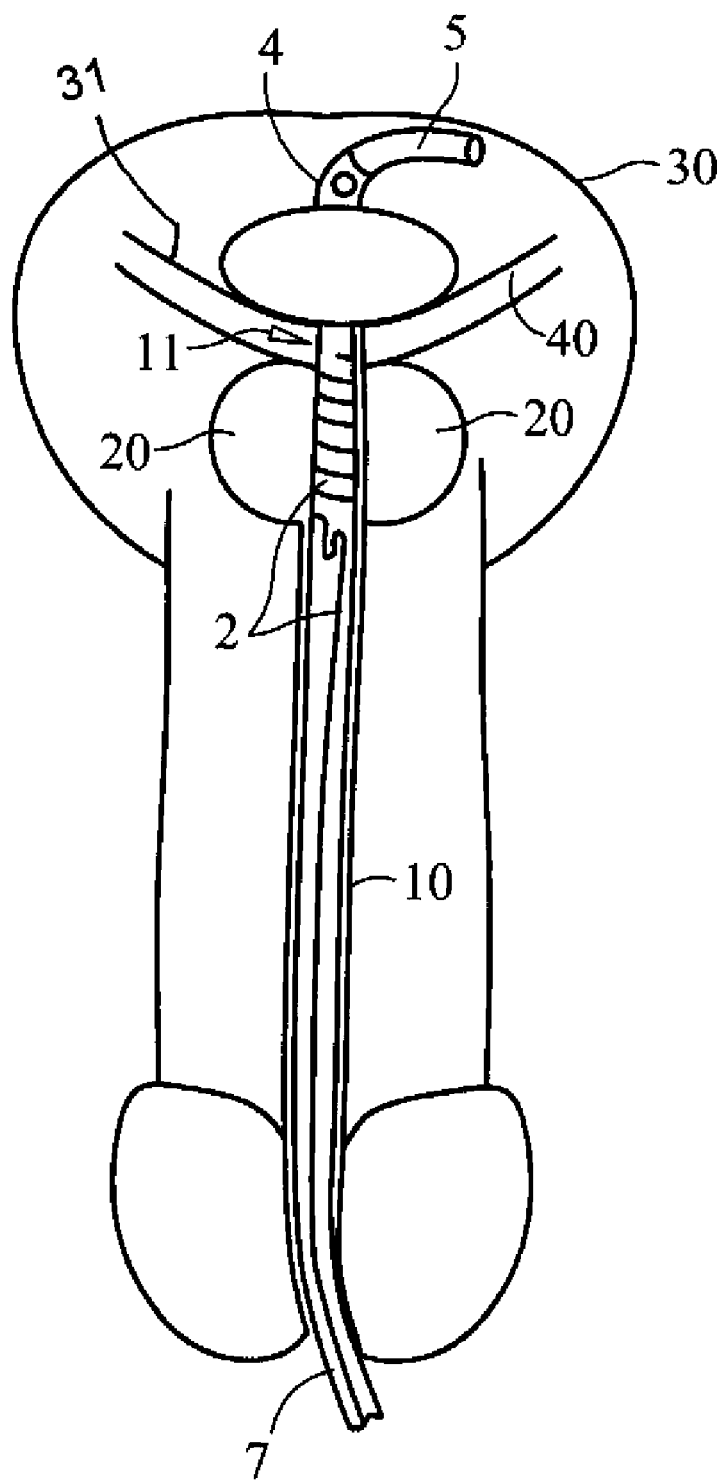
FIG. 1 is a longitudinally diagrammatic cross-sectional view of a prior art catheter ideally placed in a urethra and a bladder of a male patient.

While the specification concludes with claims defining the features of the invention that are regarded as novel, it is believed that the invention will be better understood from a consideration of the following description in conjunction with the drawing figures, in which like reference numerals are carried forward.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

Figure 2:
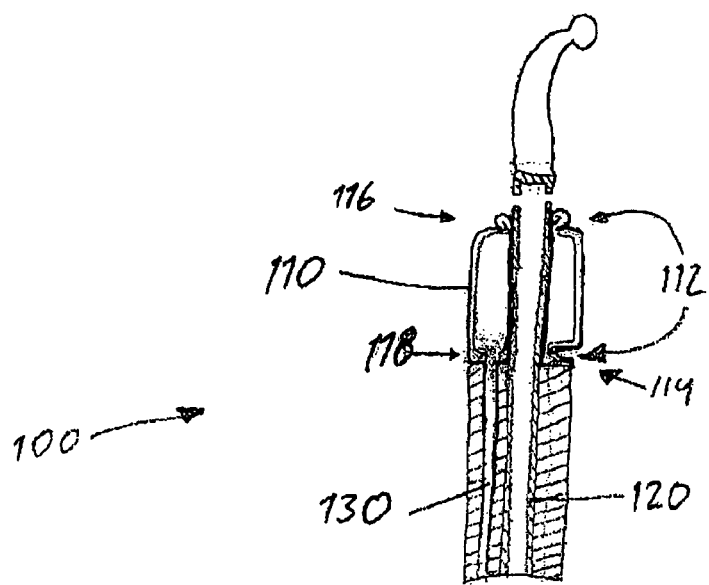
FIG. 2 is a fragmentary, enlarged, cross-sectional view of a distal portion of a first embodiment of a pressure-limiting balloon catheter according to the invention.

Referring now to the figures of the drawings in detail and first, particularly to FIG. 2 thereof, there is shown a first embodiment of a pressure-limiting balloon catheter 100 that does not inflate past the tearing limit of a lumen in which the catheter 100 is placed, for example, in the urethra.

To prevent occurrences of urethra tearing due to premature-improper inflation of the balloon and/or due to premature removal of an inflated balloon, the invention of the instant application provides the balloon 110 with a balloon safety valve 112. As set forth above, in a balloon 3 of a conventional catheter (see reference numerals 1 to 5 in FIG. 1), the balloon 3 is fixed to the outer surface of the fluid drainage line 120 (not shown in FIG. 1) and is not intended to be removed therefrom or to burst thereon unless an extraordinary amount of inflation occurs. Such a tearing event is not supposed to occur under any circumstances during use with a patient. If such an event happens, the material of the balloon 3 will open at a random location, based upon the microscopic fractures or weaknesses in the material itself, and risk of serious damage to the patient is associated with the bursting, as well as a risk of balloon fragmentation, which could leave pieces of the balloon 3 inside the patient after removal of the catheter.

In contrast to such conventional devices, the balloon 110 of the present invention is created specifically to tear when a predefined pressure exists in or is exerted on the balloon 110. The controlled tear will occur because the balloon safety valve 112 is present. Conventional balloons have constant balloon wall thicknesses. In contrast thereto, the balloon safety valve 112 in the first embodiment is a defined reduction in balloon wall thickness. This reduction creates a breaking point or selected breaking points at which the balloon 110 is intended specifically to break when a predefined force exists in or is imparted on the balloon 110. Because the balloon 110 is made of a material having a known tearing constant—dependent upon the thickness thereof (which is determined experimentally for different thicknesses of a given material prior to use in a patient), the balloon safety valve 112 of the present invention for urethra applications is matched to break when the pressure inside or exerted on the balloon 110 approaches the maximum urethra pressure.

In the embodiment shown in FIG. 2, a decreased thickness is formed as a first semi-circumferential groove 114 near a proximal end of the balloon 110 and/or as a second semi-circumferential groove 116 near a distal end of the balloon 110. The grooves 114, 116 can have any cross-sectional shape, including, trapezoidal, triangular, square, or rectangle, for example. Because rubber, plastic, and silicone materials tear well with thinner cuts, a relatively triangular shape or one with a narrow bottom is preferred. To make sure that the entire balloon 110 of the illustrated embodiment does not completely tear away from the fluid drainage line 120, both grooves 114, 116 do not extend around the entire circumference of the balloon 110. As shown to the left of the proximal groove 116 in FIG. 2, the groove 116 is not present on at least an arc portion 118 of the circumference of the balloon 110. The arc portion is defined to be sufficiently large so that, when the catheter 100 is removed from the patient, the balloon 110 cannot tear away entirely from the catheter 100 (and create the disadvantageous fragmentation situation as set forth above). The illustrated balloon safety valve 112 is, therefore, fashioned to keep the balloon 110 in one piece after breaking and firmly connected to the catheter 100 to insure that no piece of the balloon 110 will be left inside the patient after actuation of the balloon safety valve 112.

It is noted that the balloon 110 is inflated through an inflation lumen 130 having a proximal opening, typically formed by a female end of a luer connector. The female end is connected to a non-illustrated inflation device, for example, a distal end of a syringe for inflation of the balloon 110.

In this first embodiment, the balloon can be of rubber, silicone, or plastic, for example. Once the balloon breaks, the catheter is useless and must be discarded. Because the balloon 110 in this embodiment will break inside the patient, it should be inflated with a bio-safe fluid to prevent an unwanted air or gas from entering the patient. In certain circumstances where balloon catheters are used, air or gas will not injure the patient if let out into the patient's body cavity. In such circumstances, the inflating fluid can be air under pressure, for example.

Maximum urethra pressure can also be tailored to the individual patient. Based upon a urethral pressure-measuring device, the patient's maximum urethra pressure can be measured before the catheter 100 is placed therein. A set of catheters 100 having different safety valve breaking constants can be available to the physician and, after estimating or calculating or knowing the patient's maximum urethra pressure, the physician can select the catheter 100 having a safety valve breaking constant slightly or substantially smaller than the patient's maximum urethra pressure. Accordingly, if the pressure in the balloon 110 approaches the patient's maximum urethra pressure for any reason, whether it is due to over-inflation, improper placement, and/or premature removal, the balloon 110 is guaranteed to break prior to the patient's lumen, in particular, the patient's urethra, prior to causing iatrogenic injury.

Figure 3:
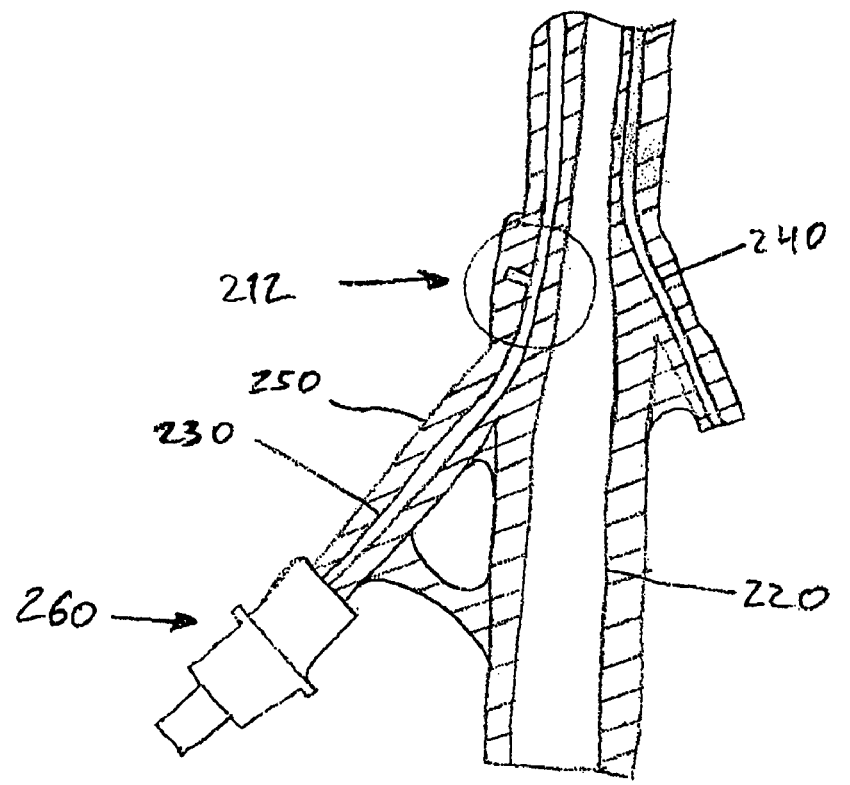
FIG. 3 is a fragmentary, enlarged cross-sectional view of a proximal portion of a second embodiment of a pressure-limiting balloon catheter according to the invention.

A second embodiment of the one-use breaking safety valve of a pressure-limiting balloon catheter 200 is shown in FIG. 3. The catheter 200 has a fluid drainage line 220, a balloon inflation lumen 230, and a secondary lumen 240.

The fluid drainage line 220 is connected fluidically to the body cavity (i.e., the bladder 30) for draining fluid from the body cavity.

The secondary lumen 240 can be used for any purpose, for example, for housing the radiation line that will supply energy to the radiation coil 2. It can also be used for injecting fluid into any distal part of the catheter 200 or even the body cavity itself.

The balloon inflation lumen 230 begins at a proximal end with an inflating connector 260 that, in a preferred embodiment, is a female luer connector (of course, it can be a male luer connector too). The balloon inflation lumen 230 continues through the body of the catheter 200 all the way to the balloon and is fluidically connected to the interior of the balloon.

The balloon safety valve is also fluidically connected to the balloon inflation lumen 230. In the second embodiment of the safety valve 212, the valve 212 is formed integrally with the balloon inflation lumen 230 and is set to open into the environment (instead of into the patient) if the maximum urethra pressure is exceeded in the balloon or the balloon inflation lumen. Because this safety valve 212 is located near or at the balloon inflation port 220 in this configuration, fluid used to inflate the balloon will not enter the patient when the valve 212 opens.

Figure 4:
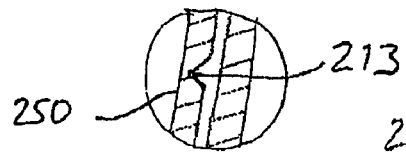
FIG. 4 is a fragmentary, enlarged, cross-sectional view of a first alternative configuration of the safety valve of FIG. 3.
Figure 5:
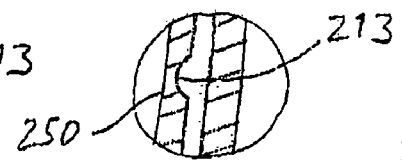
FIG. 5 is a fragmentary, enlarged, cross-sectional view of a second alternative configuration of the safety valve of FIG. 3.
Figure 6:
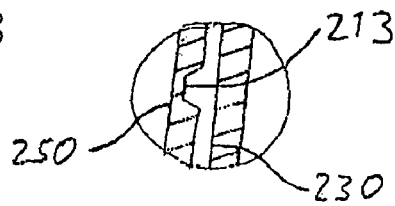
FIG. 6 is a fragmentary, enlarged, cross-sectional view of a third alternative configuration of the safety valve of FIG. 3.

The safety valve 212 in the second embodiment can merely be a narrowing of the distance between the balloon inflation lumen 230 and the outer surface 250 of the catheter 220. In FIG. 3, the valve 212 has a rectangular cross-section and extends away from the balloon inflation lumen 230. As shown in FIGS. 4, 5, and 6, respectively, the cross-section can be triangular (peaked or pyramidical in three-dimensions), curved (circular or cylindrical in three-dimensions), or trapezoidal (frusto-conical or bar-shaped in three-dimensions). The cross-sections are shown in FIGS. 3 to 7 with the narrowing emanating from the balloon inflation lumen 230 outward. As an alternative, the narrowing can begin on the outer surface of the catheter and extend inwards towards the balloon inflation lumen 230. A further alternative can have the narrowing extend from both the lumen 230 and the outer surface of the catheter.

Figure 7:
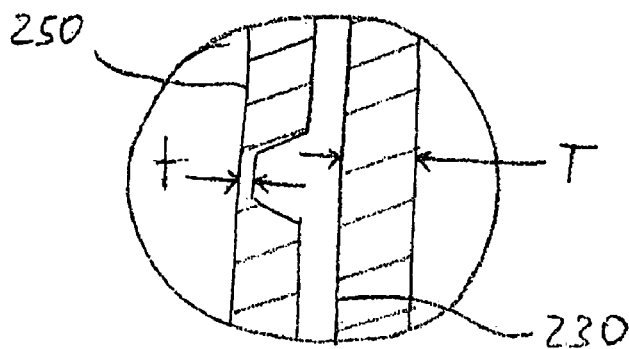
FIG. 7 is a fragmentary, further enlarged, cross-sectional view of the safety valve of FIG. 6.

The cross-sections illustrated are merely exemplary. What is important is that the thickness t between the bottom 213 of the valve 212 and the outer surface 250 of the catheter 220 in comparison to the thickness T of the catheter body over the remainder of the balloon inflation lumen 230. An enlarged view of this thickness comparison is illustrated in FIG. 7. As long as the thickness t is smaller than the thickness T (t<T), and as long as the force $F_b$ required to break the balloon is greater than the force $F_{sv}$ required to break the portion 213 of the safety valve 212 ($F_b > F_{sv}$), then the portion 213 of the safety valve 212 is virtually guaranteed to break every time pressure exerting a force F in the balloon inflation lumen 230 is greater than the force $F_{sv}$ required to break the safety valve ($F_{sv} > F$).

Based upon this analysis, the force $F_{sv}$ required to break the safety valve can be tuned to whatever a patient needs or a physician desires and different sized valves can be available for any procedure and provided in the form of a kit. Whether a standard maximum urethra pressure is used or a patient-specific maximum urethra pressure is measured and used, experiments can be conducted prior to use on a patient on various catheter thicknesses t to determine the pressure needed to break the portion 213 of the safety valve 212. For example, ten different maximum urethra pressures can be known as desirable setpoints and the thicknesses t can be varied such that pressure required to break the ten thicknesses correspond to the ten setpoint pressures. If, then, ten catheters are placed in such a kit, each having one of the ten thicknesses, then the physician has a range of 10 maximum urethra pressure values to use with the patient.

The safety valve 212 of the second embodiment need not be confined to the body of the catheter 200. Instead, the inflating connector 260 can be equipped with the safety valve 212. Alternatively, a modular attachment 270 containing the safety valve 212 can be attached to the inflating connector 260. Such a modular valve attachment 270 is removable and replaceable (such as through a convention luer or even a screw-threaded connection). Accordingly, as long as the catheter 200 can still be used after the valve 212 actuates (breaks), the used attachment 270 can be replaced with a new attachment 270. The converse is also true for reuse of the attachment 270 if the catheter 200 breaks and the valve of the attachment 270 remains unbroken.

Figure 9:
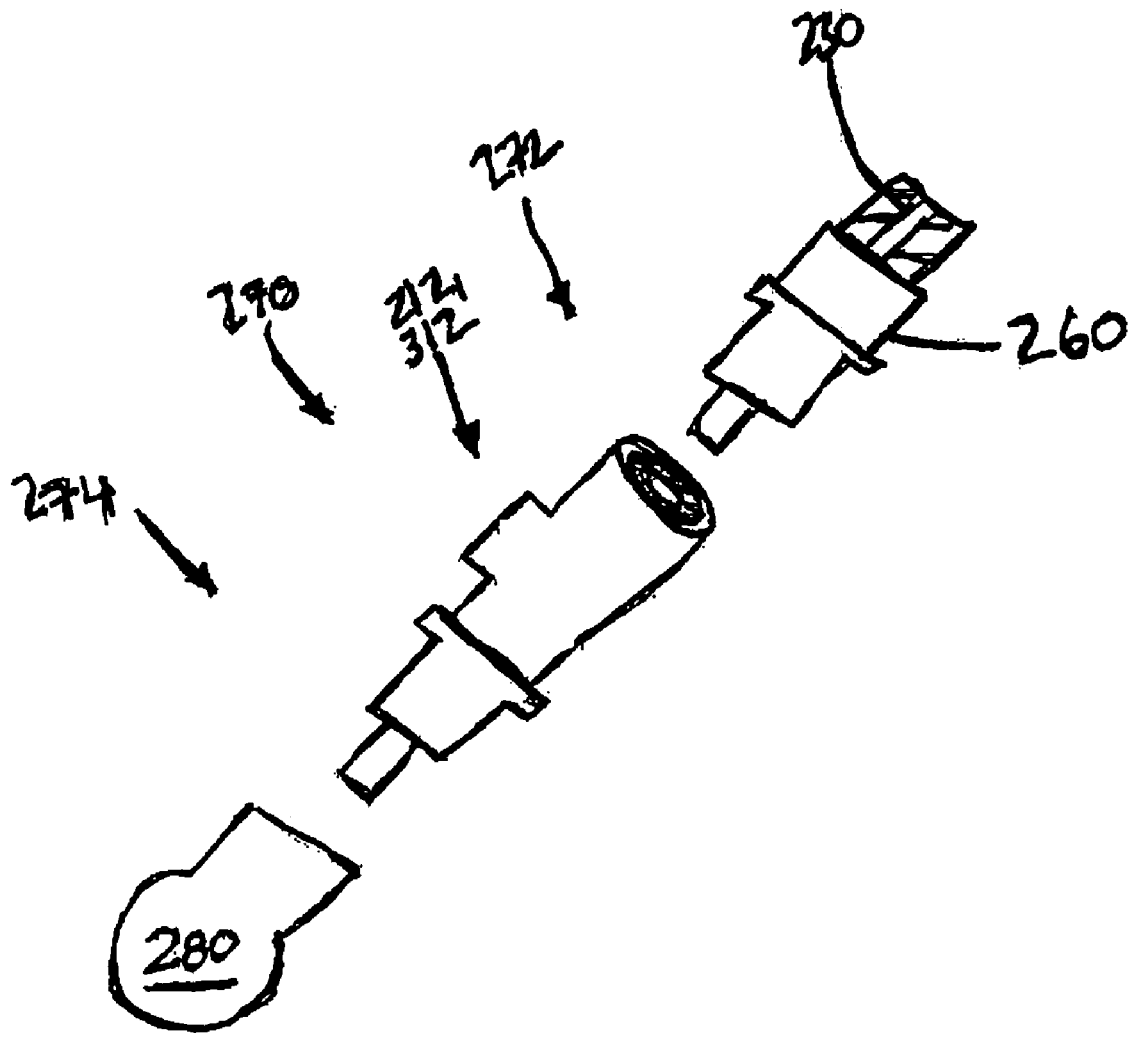
FIG. 9 is a fragmentary, perspective view of a fifth alternative configuration of a retrofitting safety valve according to the invention.

One embodiment of the attachment is illustrated in FIG. 9. Specifically, an upstream end of the connector 260 is attached removably to a downstream end 272 of the modular valve attachment 270 and the upstream end 274 of the attachment 270 is attached to the female connection of the balloon inflation device 280 illustrated only diagrammatically in FIG. 9. A common exemplary inflation device 280 is a syringe.

In such a configuration, the safety valve 212, 312 of the present invention can be entirely separate from the catheter 200, 300 and, therefore, form a retrofitting device for attachment to the luer connector present on conventional catheters.

Figure 8:
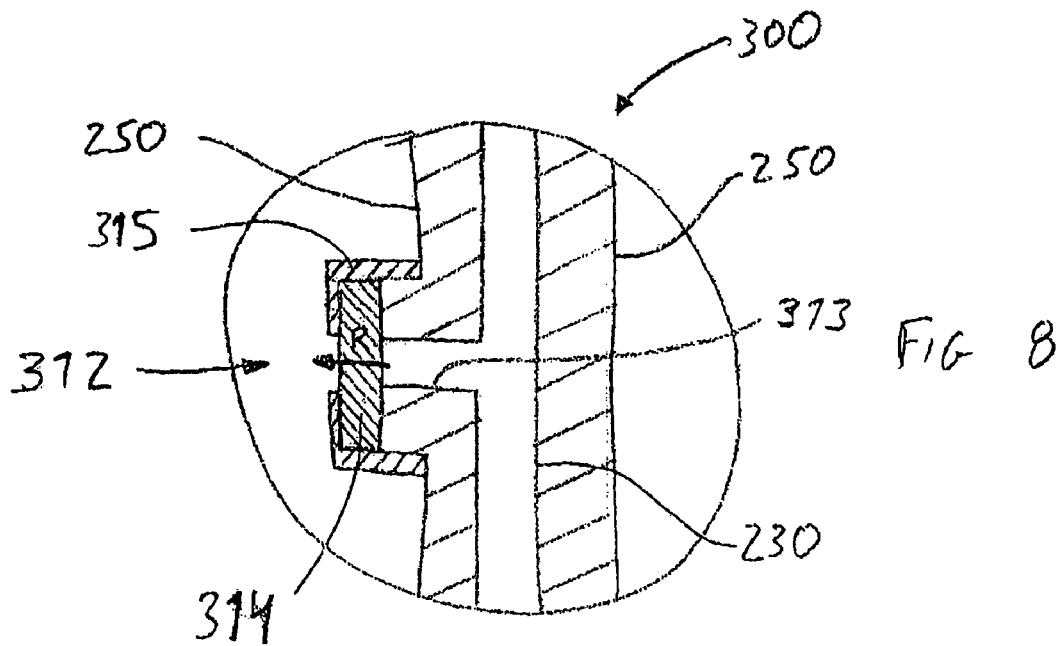
FIG. 8 is a fragmentary, further enlarged, cross-sectional view of a fourth alternative configuration of the safety valve of FIG. 3.

As an alternative to the one-use breaking safety valve of the second embodiment, a multi-use pressure valve can be used. This third embodiment of the pressure-limiting balloon catheter 300 is illustrated in FIG. 8. The catheter 300 can be the same as the catheter 200 in FIG. 3 except for the portion illustrated in FIG. 8. Instead of having a narrowing thickness t of the lumen wall, the valve portion 313 extends entirely to the environment. However, a one-way valve 314 (shown only diagrammatically in FIG. 8) is attached to the open end of the valve portion 313 and is secured to the outer surface 250 of the catheter 300 to close off the open end of the valve portion 313. The one-way valve 314 can be secured directly to the outer surface 250 (e.g., with an adhesive) or a connector 315 (e.g., a threaded cap) can secure the one-way valve 314 to the open end of the valve portion 313. Regardless of the configuration, the one-way valve 314 includes a device that does not permit fluid from exiting the lumen 230 until a given resistance R is overcome. This given resistance R can be selectable by the physician depending upon the one-way valve that is chosen for use if a set of one-way valves having different resistances R are available for use by the physician. Just like the second embodiment, the resistance R can be set to correspond to desired maximum urethra pressure values. Therefore, when used, the fluid exits the one-way valve 314 into the environment well before the patient's maximum urethra pressure is exceeded by the balloon.

The one-way valve 314 can be a mechanical one-way valve. Additionally, the one-way valve 314 can be a material having a tear strength corresponding to the desired set of resistances R. The material can be a fluid-tight fabric, a rubber, a plastic, or silicone different from the material making up the catheter. The material can even be a rubber, plastic, or silicone the same as the material making up the catheter but having a reduced thickness t than the thickness T of the catheter.

Because the safety valve 212, 312 is located at the proximal end of the catheter 200, 300, the distal end of the catheter 200, 300 can take the form of a distal end of a conventional balloon catheter 2, 3, 4, 5. Alternatively, the distal end shown in FIG. 2 can also be used for redundant over-pressure protection.

The catheter 200, 300 according to the invention can be used in vascular applications. It is known that every vessel has a tearing pressure. Balloons are used in coronary arteries, for example. If a coronary artery balloon were to burst, there would be less damage if the burst was controlled according to the invention. The same is true for a renal or iliac blood vessel. In such situations, the breakaway catheter improves upon existing catheters by making them safer. From the urinary standpoint, the breakaway balloon will not only prevent injury, but will also be a signal to the technician that he/she needs to obtain the assistance of a physician or urologist with respect to inserting the catheter.

Figure 10:
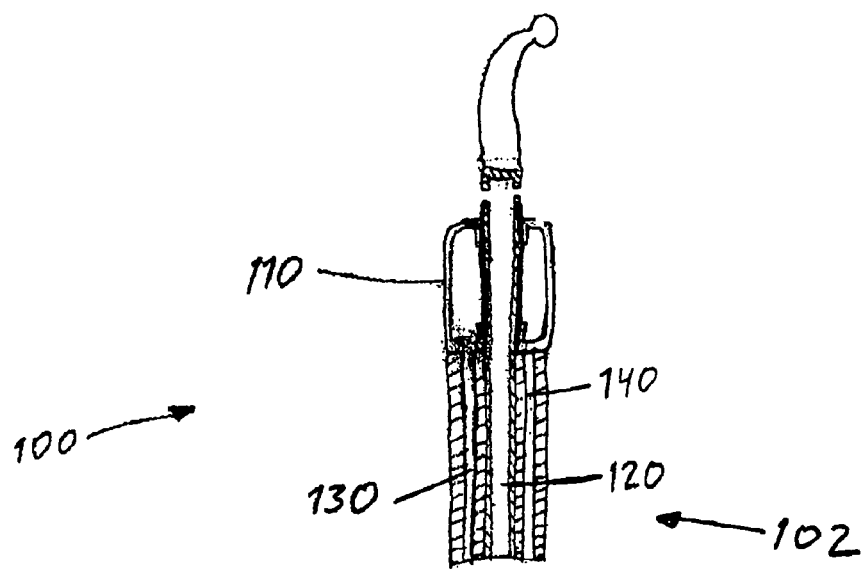
FIG. 10 is a fragmentary, enlarged, cross-sectional view of a distal portion of a first embodiment of an illuminating balloon catheter according to the invention.

Referring now to FIG. 10 thereof, there is shown a first embodiment of an illuminating balloon catheter 100 having a distal balloon 110, a catheter body 102, and a drainage assembly 150.

The catheter body 102 defines a fluid drainage lumen 120, a balloon inflating lumen 130, and an illumination device lumen 140.

The distal end of the drainage assembly 150 is explained below with regard to FIG. 12 and includes a shaft on which or around which the balloon 110 is connected. The drainage assembly 150 has at least one distal drainage port 152 at the proximal end of the catheter 100 for draining fluid from a body cavity (i.e., urine from a bladder). The drainage assembly 150 can also be integral with or connected to the catheter tip 154.

The interior of the balloon 110 is fluidically connected to the balloon inflating lumen 130. The balloon 110 is inflated through a connector 160 disposed at a proximal opening 132 of the inflation lumen 130. See FIG. 11. Typically, a female end of a luer connector forms the connector 160 and is shaped to connect to a non-illustrated inflation device, for example, a distal end of a syringe for inflation of the balloon 110.

Figure 11:
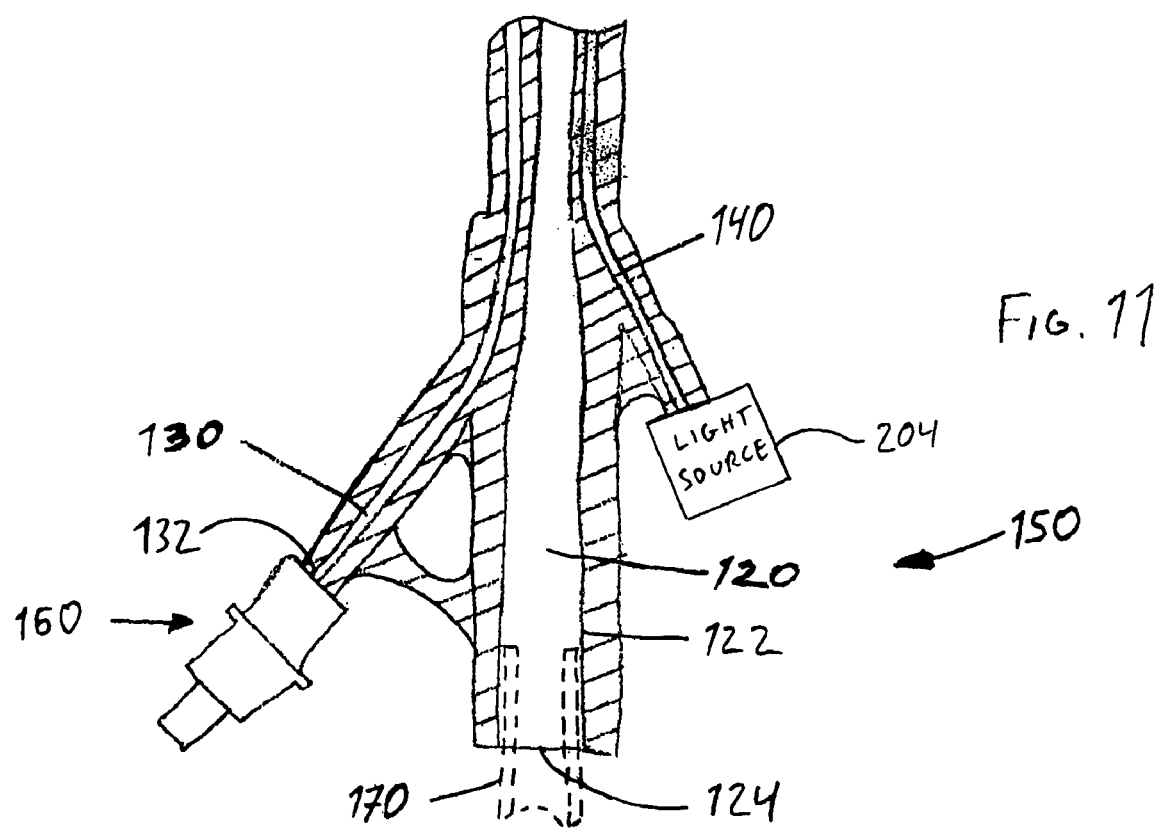
FIG. 11 is a fragmentary, enlarged cross-sectional view of a proximal portion of the catheter of FIG. 10.

FIG. 11 illustrates an exemplary embodiment of the proximal end of the catheter 100 of the present invention. The proximal end includes the proximal portions of the fluid drainage lumen 120, the balloon inflation lumen 130, and the illumination device lumen 140.

The fluid drainage lumen 120 is fluidically connected at a proximal end thereof to a drainage device having a drainage funnel 122 defining a proximal, substantially circular opening 124 within which is received a fluid connection device 170, indicated in FIG. 11 diagrammatically with dashed lines.

The balloon inflation lumen 130 begins at a proximal end with the inflating connector 160, continues through the body 102 of the catheter 100 all the way distal to the balloon 110 and is fluidically connected to the interior 112 of the balloon 110 as set forth above.

The illumination device lumen 140 is formed to house a directional illumination source 201, shown (in a first embodiment in FIG. 12) as a fiber optic strand having a distal end 202 terminating flush with a transparent portion of the balloon 110. This strand supplies light into the balloon 110. Thus, all of the light emanating from the distal end 202 of the strand is coupled into the cavity 112 of the balloon 110. A conventional fiber optic light source can be coupled to the fiber optic strand and, therefore, is not described in further detail nor is it illustrated more than diagrammatically with box 204 in FIG. 11.

Without anything further, if the balloon 110 were entirely transparent, the light entering the balloon 110 would enter the cavity 112 and pass entirely through the balloon 110 out the distal side thereof. The present invention, however, provides a reflective surface 210 on the balloon 110. The reflective surface 210 is shown on the interior of the balloon 110, however, it can be on the exterior of the balloon 110 as well. The reflective surface 210 can be a coating thereon or it can be a natural property of the material making up the balloon 110.

Figure 12:
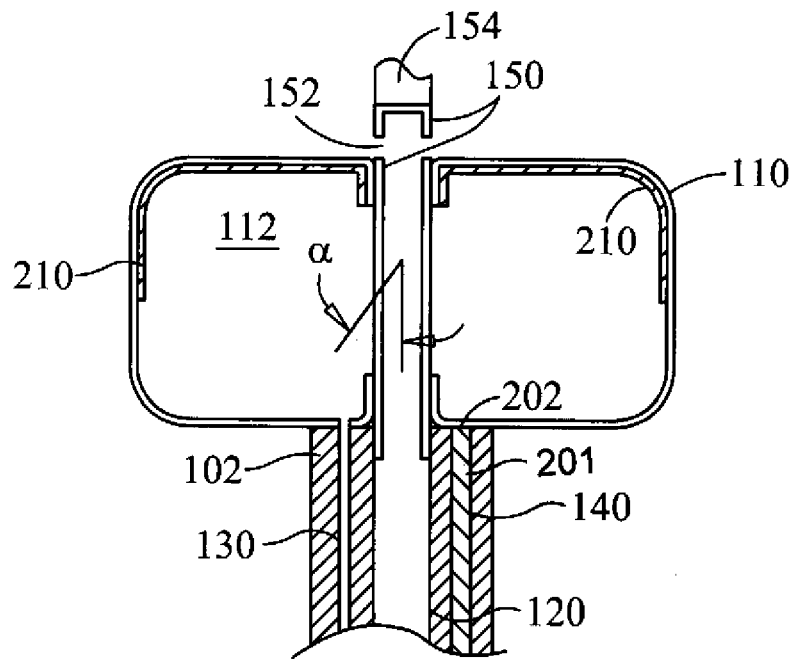
FIG. 12 is a fragmentary, enlarged, cross-sectional view of a first configuration of a reflective balloon of the catheter of FIGS. 10 and 11.

In FIG. 12, the reflective surface 210 is shown covering approximately half of the interior surface of the balloon 110, i.e., it is substantially hemispherical. Thus, the light will emanate from the balloon 110 over the proximal hemispherical half and only illuminate structure located on the proximal side of the balloon 110 (below the balloon in FIG. 12). This configuration, however, is merely exemplary because the reflective surface 210 can be fashioned to traverse any extent on the balloon 110. Also, it need not be symmetrical.

In the hemispherical shape of FIG. 12, the reflective surface forms a concave mirror and, therefore, focuses light in the proximal direction. Alternatively, the reflective surface can be formed asymmetrically to focus and/or direct light at any angle $\alpha$ with respect to the longitudinal extent of the catheter body 102.

Figure 13:
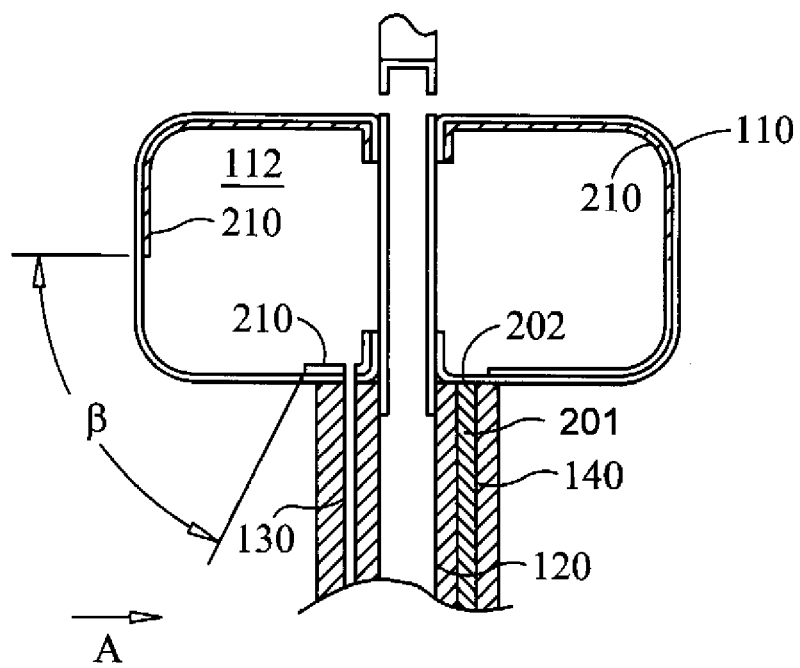
FIG. 13 is a fragmentary, enlarged, cross-sectional view of a second configuration of a reflective balloon of the catheter of FIGS. 10 and 11.

As shown, for example, in FIG. 13, the reflective surface 210 is disposed on substantially all of the right half of the balloon 110 and is disposed on the distal half of the left side of the balloon 110 and on a portion adjacent the exit of the balloon inflating lumen 130. In this configuration, the light coupled into the balloon 110 from the distal end 202 is reflected and emanates from the balloon 110 opposite the illuminating source 200 over an arc-shaped area $\beta$. Thus, if the physician is located on the left side of the catheter 100 with respect to FIG. 13, and is looking at the catheter 100 in a direction along arrow A, all of the light will be emerging on the side facing the physician and in a relatively proximal direction. Such illumination is very beneficial when locating the urethrovesical junction in a laparoscopic prostatectomy.

Figure 14:
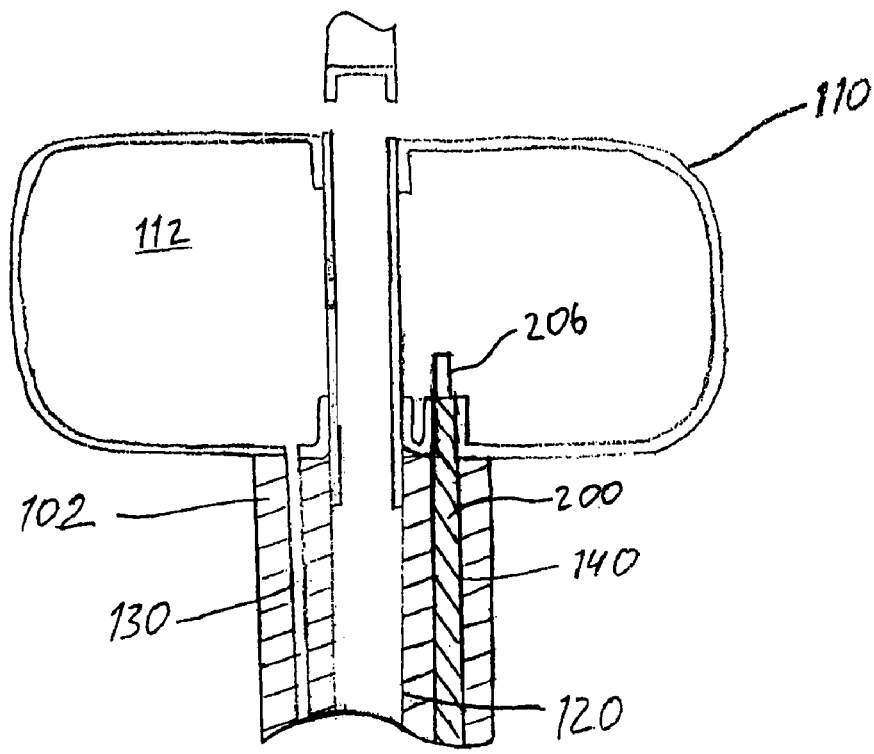
FIG. 14 is a fragmentary, enlarged, cross-sectional view of a second embodiment of the illuminating balloon catheter according to the invention.

A second embodiment of the illuminating balloon catheter is shown in FIG. 14. Therein, the illuminating device 200 (e.g., a fiber optic strand) is shielded from emitting illumination up until a point at which it emerges into the cavity 112 of the balloon 110. This unshielded portion 206 allows the light to enter the balloon 110 without be attenuated by the material of the balloon 110, which occurs to a small extent in the first embodiment. One drawback to this second embodiment is that two holes need to be created in the balloon 100 because the illumination source 200 is in a lumen entirely separate from the balloon inflation lumen 130.

Figure 15:
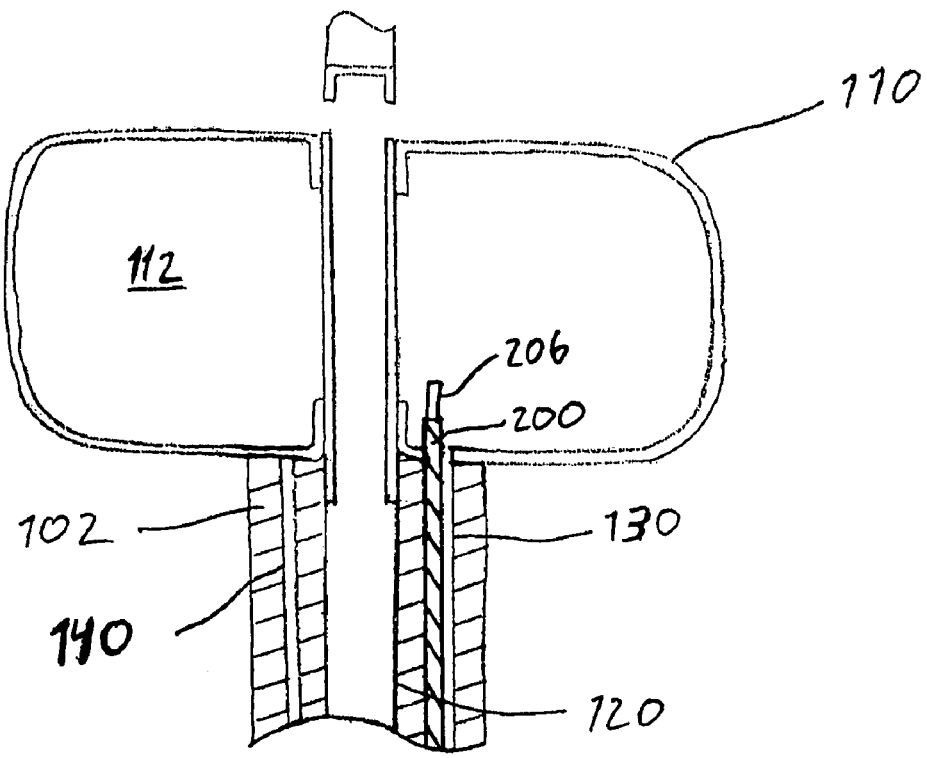
FIG. 15 is a fragmentary, enlarged, cross-sectional view of a third embodiment of the illuminating balloon catheter according to the invention.

If, however, the balloon inflation lumen 130 is sufficiently large to fit therein the illumination source 200 (in a fluid-tight fit at the proximal end of the lumen 130) and still allow inflation of the balloon 110 without substantial back pressure or closing off of the lumen 130, then the balloon 110 can be formed with only one hole. Such an alternative configuration is shown in FIG. 15. In this configuration, the secondary lumen 140 becomes available for another useful purpose.

Figure 16:
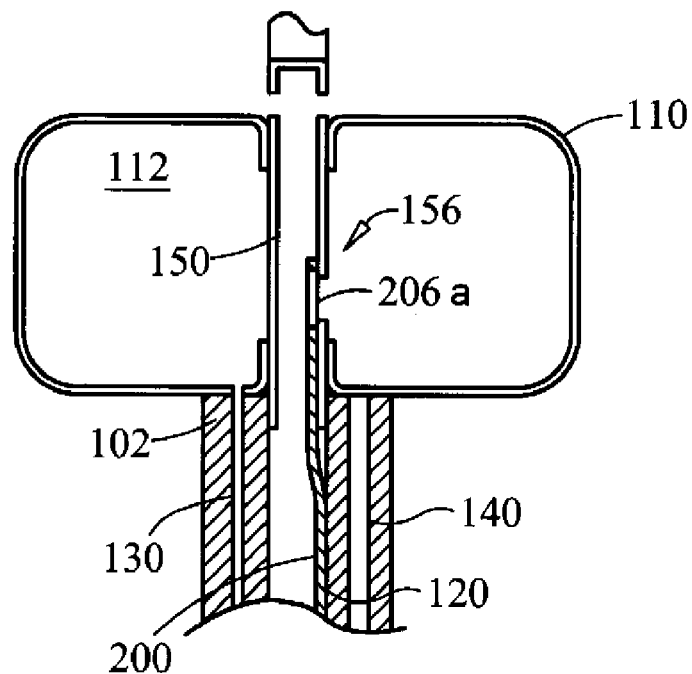
FIG. 16 is a fragmentary, enlarged, cross-sectional view of a fourth embodiment of the illuminating balloon catheter according to the invention.

FIG. 16 illustrates a fourth alternative embodiment of the illuminating balloon catheter 100. Specifically, the illuminating device 200 (e.g., fiber optic) is led through the fluid drainage lumen 120 and is fastened to the inside surface thereof except for a distal-most portion near the point at which the drainage assembly 150 is secured. The drainage assembly 150 is formed with an intermediate opening 156 that can be fluid-tightly sealed by securing thereto the unshielded portion 206 of the fiber optic device 200, for example. This embodiment is particularly suited for an LED as the illumination source because the intermediate opening 156 can be formed with exact tolerances so that the LED can be secured therein easily in a fluid-tight manner with conventional glues.

Figure 17:
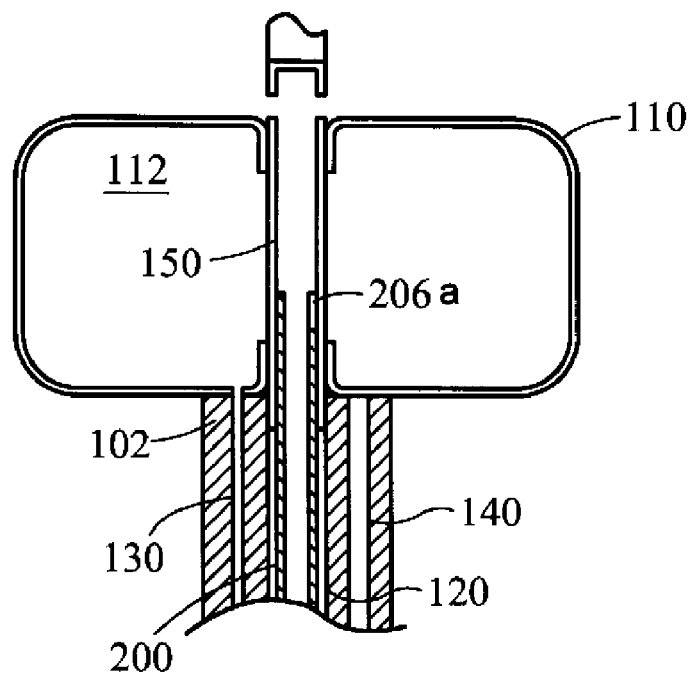
FIG. 17 is a fragmentary, enlarged, cross-sectional view of a fifth embodiment of the illuminating balloon catheter according to the invention.

FIG. 17 illustrates a fifth alternative embodiment of the illuminating balloon catheter 100. Specifically, the illuminating device 200 is tubular and is led through the fluid drainage lumen 120 in a longitudinally movable manner. The illuminating device 200 has a distal-most portion at which is disposed an illuminator 206a. The illuminator 206a can be formed from an unshielded portion of a fiber optic or can be an LED having an illumination direction disposed along a radial line orthogonal to the longitudinal extent of the illuminating device 200. Because the illuminating device 200 can be rotated 360 degrees inside the fluid drainage lumen 120, a portion of the drainage assembly 150 inside the balloon is transparent. Thus, as the illuminator 206a is rotated within the fluid drainage lumen 120, the light beam also rotated within the balloon. In this embodiment, therefore, the catheter need not be rotated inside the patient's urethra. To make sure that a majority of the illumination is directed proximally, the balloon 110 is, in this fifth embodiment, provided with the hemispherical reflector 210 similar to that shown FIG. 12 (but not shown in FIG. 17). It is noted that the hollow structure of the illuminating device 200 allows for virtually unhindered passage of the fluid that is to be drained through the fluid drainage lumen 120.

Laparoscopic prostatectomy can be assisted with all of the configurations shown in FIGS. 12 to 17. With the invention of the instant application, the balloon of the catheter is inflated in the bladder and the surgeon or assistant directs the light to help locate the urethrovesical junction. Inflation of the balloon such that the proximal portion thereof presses against the proximal wall of the bladder near the urethrovesical junction to compress the tissue at the urethrovesical junction. Such compression allows the urethrovesical junction to be very apparent when viewed through a laparoscope. The directed illumination from the illumination device 200, in combination with the compression of the urethrovesical junction, allows the metes and bounds of the urethrovesical junction to be clearly identified. Accordingly, a laparoscopic prostatectomy can have greater chances for success.

A fiber optic is used herein as an illustrative example for the illumination source. It should not, however, be deemed as limiting the scope of potential illumination sources. For example, as set forth above, conventional light-emitting diodes (LEDs) can be used. Also, printed organic light-emitting diodes (OLEDs) can be used both as the illumination source and as the reflective coating. Specifically, if the feature shown as a reflective coating 210 in FIGS. 4 and 5 is substituted with a printed OLED, then the OLED can become an illumination source that does not need reflection to direct illumination from the balloon 110 of the present invention. Other similar forms of illumination devices can be substituted or used.

The breakaway catheter is not only a separate device from the illuminating catheter and vice-versa. Therefore, it is envisioned that the two catheters described individually herein can be combined in any manner into a single catheter with any of the features of both.

We claim:

1. A directionally illuminating balloon catheter, comprising:
    a multi-lumen shaft having a distal end, said shaft defining:
        a fluid drain lumen; and
        a balloon inflation lumen; and
    a hollow balloon having a proximal side disposed at said distal end to define a shaft-balloon junction, said balloon defining an interior fluidically connected to said balloon inflation lumen and inflated through said balloon inflation lumen, said balloon comprising:
        an integrated light source;
        a non-reflective surface adjacent said shaft-balloon junction; and
        a reflective surface disposed at a portion of said balloon other than said non-reflective surface such that said integrated light source illuminates only a proximal half of the environment outside said balloon.

2. The catheter according to claim 1, wherein said light source is connected to said interior of said balloon through at least one of said fluid drain lumen and said balloon inflation lumen.

3. The catheter according to claim 1, wherein said shaft further defines an illumination device lumen and said light source is connected to said interior of said balloon through said illumination device lumen.

4. The catheter according to claim 1, wherein:
    said shaft has a proximal end defining a balloon port fluidically connected to said balloon inflation lumen; and
    an inflating connector is fluidically connected to said balloon inflation lumen through said balloon port.

5. The catheter according to claim 4, wherein said inflating connector is at least a portion of a luer connector.

6. The catheter according to claim 4, wherein said proximal end of said shaft defines a fluid port fluidically connected to said fluid drain lumen.

7. The catheter according to claim 6, wherein:
    said balloon has a distal end; and
    a fluid drain is disposed at said distal end of said balloon and fluidically connects said fluid drain lumen to the environment at said distal end of said balloon.

8. The catheter according to claim 7, wherein said fluid drain has a curved, distal guiding tip.

9. The catheter according to claim 1, wherein said non-reflective surface and said reflective surface define regions of said balloon having different reflectivity and opaqueness to direct illumination from within said balloon into a given area outside said balloon.

10. The catheter according to claim 1, wherein said balloon is of a material and said non-reflective surface and said reflective surface are a natural property of said material.

11. The catheter according to claim 1, wherein said non-reflective surface comprises an at least semi-transparent portion for transmitting light out from said balloon through said at least semi-transparent portion, and said reflective surface comprises an opaque portion for preventing transmission of light out from said balloon through said opaque portion.

12. The catheter according to claim 1, wherein:
    said shaft and said balloon form a urethral catheter; and
    said light source illuminates substantially only a urethrovesical junction when said proximal side of said balloon is adjacent the urethrovesical junction.

13. The catheter according to claim 1, wherein said light source is at least one of inside and outside said balloon.

14. The catheter according to claim 1, wherein said reflective surface comprises a reflective coating to direct light emanating from said balloon.

15. The catheter according to claim 14, wherein said coating is integral with said balloon.

16. The catheter according to claim 14, wherein said coating is disposed on said balloon.

17. The catheter according to claim 1, wherein said light source directs substantially all illumination towards said shaft.

18. The catheter according to claim 1, wherein said light source transmits substantially no illumination out from said balloon opposite said shaft.

19. The catheter according to claim 1, wherein said light source rotates within said interior of said balloon.

20. The catheter according to claim 19, wherein said light source directs light only in a given direction.

21. The catheter according to claim 1, wherein said light source is selected from at least one of the group consisting of a fiber optic, a light-emitting diode, an organic light-emitting diode, and a combination of said fiber optic, said light-emitting diode, and said organic light-emitting diode.

22. A directionally illuminating balloon catheter kit, comprising:
a set of catheters according to claim 1, each of said catheters having said light source with different sized illuminating areas to illuminate a different sized partial portion of the environment outside said balloon.

23. A directionally illuminating balloon catheter, comprising:
a multi-lumen shaft having a distal end, said shaft defining:
a fluid drain lumen; and
a balloon inflation lumen; and
a hollow balloon having a proximal side disposed at said distal end to define a shaft-balloon junction, said balloon defining an interior fluidically connected to said balloon inflation lumen and inflated through said balloon inflation lumen, said balloon comprising:
an integrated light source;
a non-reflective surface adjacent said shaft-balloon junction; and
a reflective surface disposed at a portion of said balloon other than said non-reflective surface such that said integrated light source illuminates only approximately half of the proximal half of the environment outside said balloon.

24. A directionally illuminating balloon catheter, comprising:
a multi-lumen shaft having a distal end, said shaft defining:
a fluid drain lumen; and
a balloon inflation lumen; and
a hollow balloon having a proximal side disposed at said distal end to define a shaft-balloon junction, said balloon defining an interior fluidically connected to said balloon inflation lumen and inflated through said balloon inflation lumen, said balloon comprising:
an integrated light source;
a non-reflective surface adjacent said shaft-balloon junction; and
a reflective surface disposed at a portion of said balloon other than said non-reflective surface such that said integrated light source illuminates only a partial asymmetrical proximal portion of the environment outside said balloon.

25. A directionally illuminating balloon catheter, comprising:
a multi-lumen shaft having a distal end, said shaft defining:
a fluid drain lumen; and
a balloon inflation lumen; and
a hollow balloon having a proximal side disposed at said distal end to define a shaft-balloon junction, said balloon defining an interior fluidically connected to said balloon inflation lumen and inflated through said balloon inflation lumen, said balloon comprising:
an integrated light source,
a non-reflective surface adjacent said shaft-balloon junction; and
a reflective surface disposed at a portion of said balloon other than said non-reflective surface such that said integrated light source is limited in direction towards said proximal side of said balloon.

26. A directionally illuminating balloon catheter, comprising:
a multi-lumen shaft having a distal end, said shaft defining:
a fluid drain lumen; and
a balloon inflation lumen; and
a hollow balloon having a proximal side disposed at said distal end to define a shaft-balloon junction, said balloon defining an interior fluidically connected to said balloon inflation lumen and inflated through said balloon inflation lumen, said balloon comprising:
an integrated light source;
a non-reflective surface adjacent said shaft-balloon junction; and
a reflective surface disposed at a portion of said balloon other than said non-reflective surface such that said integrated light source directs substantially all illumination towards said shaft.

* * * * *

UNITED STATES PATENT AND TRADEMARK OFFICE
CERTIFICATE OF CORRECTION

Page 1 of 1

PATENT NO. : 7,883,503 B2
APPLICATION NO. : 11/339258
DATED : February 8, 2011
INVENTOR(S) : Gary Kalser and Gregory L. Mayback It is certified that error appears in the above-identified patent and that said Letters Patent is hereby corrected as shown below:

Title Page, Item (75) Inventors
The first named inventor's last name should read --Kalser--.

Title Page, Item (57)
In the Abstract, line 6, delete the word "be".

Signed and Sealed this
Nineteenth Day of April, 2011

David J. Kappos
*Director of the United States Patent and Trademark Office*